United States Patent
Hirotsu

(10) Patent No.: US 12,019,068 B2
(45) Date of Patent: Jun. 25, 2024

(54) METHOD FOR PREDICTING THERAPEUTIC EFFECT AND/OR RECURRENCE MONITORING IN CANCER PATIENTS

(71) Applicants: HIROTSU BIO SCIENCE INC., Minato-ku (JP); NANPUH HOSPITAL, Kagoshima (JP)

(72) Inventor: Takaaki Hirotsu, Tokyo (JP)

(73) Assignees: HIROTSU BIO SCIENCE INC., Chiyoda-ku (JP); NANPUH HOSPITAL, Kagoshima (JP)

(*) Notice: Subject to any disclaimer, the term of this patent is extended or adjusted under 35 U.S.C. 154(b) by 487 days.

(21) Appl. No.: 16/498,895

(22) PCT Filed: Mar. 30, 2018

(86) PCT No.: PCT/JP2018/013578
§ 371 (c)(1),
(2) Date: Sep. 27, 2019

(87) PCT Pub. No.: WO2018/181881
PCT Pub. Date: Oct. 4, 2018

(65) Prior Publication Data
US 2020/0400653 A1 Dec. 24, 2020

(30) Foreign Application Priority Data
Mar. 31, 2017 (JP) .................. 2017-069733

(51) Int. Cl.
*G01N 33/483* (2006.01)
*G01N 33/50* (2006.01)

(52) U.S. Cl.
CPC ..... *G01N 33/5085* (2013.01); *G01N 33/5011* (2013.01)

(58) Field of Classification Search
None
See application file for complete search history.

(56) References Cited

U.S. PATENT DOCUMENTS

| | | |
|---|---|---|
| 2005/0202521 A1 | 9/2005 | Crum |
| 2007/0196876 A1 | 8/2007 | Moses et al. |
| 2008/0091085 A1 | 4/2008 | Urushihata et al. |
| 2008/0118432 A1 | 5/2008 | Bergstein et al. |
| 2010/0105067 A1 | 4/2010 | Fung et al. |
| 2010/0198521 A1 | 8/2010 | Haick |
| 2011/0081650 A1 | 4/2011 | Moses et al. |
| 2014/0242616 A1 | 8/2014 | Moses et al. |
| 2016/0377624 A1 | 12/2016 | Ohrvik et al. |
| 2017/0016906 A1 | 1/2017 | Hirotsu et al. |
| 2017/0082631 A1 | 3/2017 | Moses et al. |
| 2017/0089906 A1 | 3/2017 | Fung et al. |
| 2017/0146536 A1 | 5/2017 | Bergstein et al. |
| 2017/0260284 A1 | 9/2017 | Matsumura et al. |
| 2017/0281725 A1 | 10/2017 | Sims et al. |
| 2018/0238896 A1 | 8/2018 | Moses et al. |
| 2018/0364237 A1 | 12/2018 | Bergstein et al. |
| 2019/0361028 A1 | 11/2019 | Moses et al. |

FOREIGN PATENT DOCUMENTS

| | | |
|---|---|---|
| CA | 3 057 970 A1 | 10/2018 |
| CN | 101421622 A | 4/2009 |
| CN | 103882118 A | 6/2014 |
| CN | 106255877 A | 12/2016 |
| EP | 3 081 935 A1 | 10/2016 |
| JP | 2010-266386 A | 11/2010 |
| JP | 2015-83981 A | 4/2015 |
| JP | 2015-92192 A | 5/2015 |
| JP | 2016-95233 A | 5/2016 |
| KR | 10-2016-0095135 A | 8/2016 |
| WO | WO 2006/046588 A1 | 5/2006 |
| WO | WO 2015/088039 A1 | 6/2015 |
| WO | WO 2015/118023 A1 | 8/2015 |
| WO | WO 2016/039321 A | 3/2016 |
| WO | WO 2016/044041 A1 | 3/2016 |
| WO | WO 2018/181869 A1 | 10/2018 |

OTHER PUBLICATIONS

Extended European Search Report dated Feb. 3, 2021 in European Patent Application No. 18776283.6, 9 pages.
Kusumoto, H., et al., "Behavioural Response Alteration in *Caenorhabditis elegans* to urine After Surgical Removal of Cancer: Nematode-NOSE (N-NOSE) for Postoperative Evaluation", Biomarkers in Cancer, vol. 11, 2019, pp. 1-7.
Chinese Office Action dated Mar. 3, 2021 in Chinese Patent Application No. 201888018983.8, 6 pages.
Combined Chinese Office Action and Search Report dated Mar. 3, 2020, in Patent Appliction No. 2018800189683.8, 9 pages (with English Translation of Category of Cited Documents).
Hirotsu, T. et al., "A Highly Inclusive Cancer Screening Test Using *Caernorhebditis elegans* Scent Detection", PLOS one, vol. 10, No. 3, Mar. 11, 2015, 15 pages.
International Search Report dated Jul. 3. 2018 in PCT/JP2018/013578 filed Mar. 30, 2018.
Alsadius, D. et al., "Perception of body odor—an overlooked consequence of long-term gastrointestinal and urinary symptoms after radiation therapy for prostate cancer," Journal of Cancer Survivorship, vol. 7, No. 4, Aug. 23, 2013, pp. 652-658.
Japanese Office Action dated Apr. 21, 2020 in Patent Application No. 2019-510235, 4 pages.

*Primary Examiner* — Celine X Qian
(74) *Attorney, Agent, or Firm* — Oblon, McClelland, Maier & Neustadt, L.L.P.

(57) ABSTRACT

The present invention provides a method for predicting a therapeutic effect and/or monitoring recurrence in a cancer patient. Disclosed is a method for detecting a therapeutic effect of cancer treatment in a cancer patient, comprising: measuring nematode tactic behavior to each of pre-treatment urine and in-treatment or post-treatment urine from the cancer patient; and comparing a result of measuring the tactic behavior to the pre-treatment urine and a result of measuring the tactic behavior to the in-treatment or post-treatment urine, wherein when attraction is weakened or avoidance is strengthened after the treatment, it is determined that the therapeutic effect is detected.

3 Claims, 1 Drawing Sheet

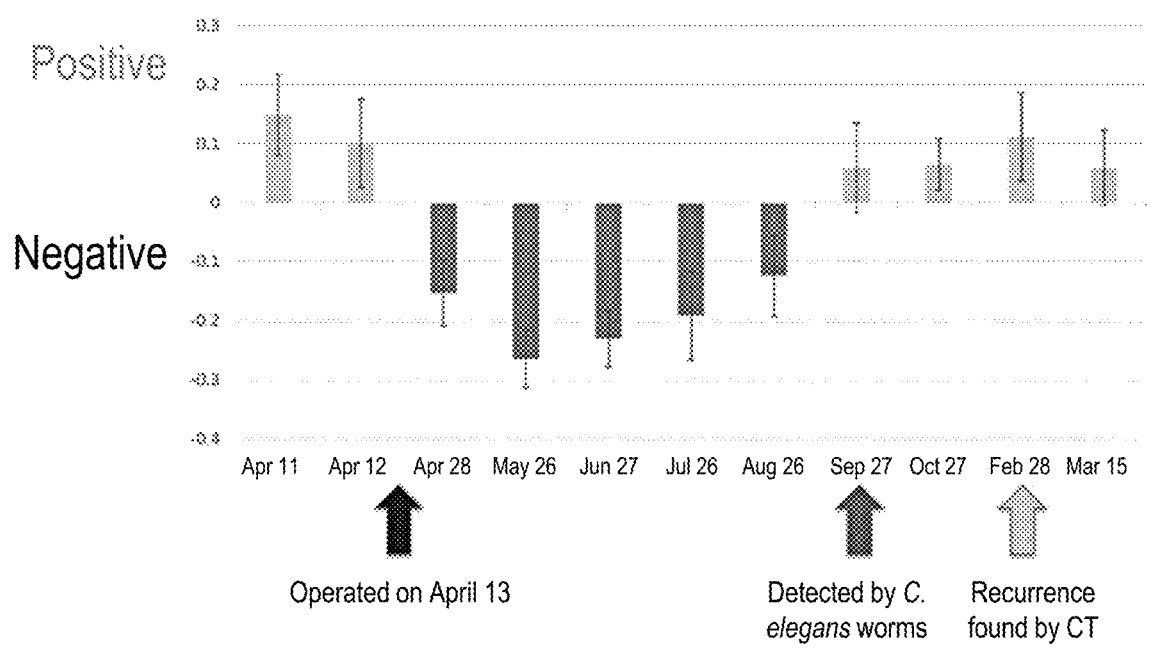

US 12,019,068 B2

METHOD FOR PREDICTING THERAPEUTIC EFFECT AND/OR RECURRENCE MONITORING IN CANCER PATIENTS

TECHNICAL FIELD

The present invention relates to a method for predicting a therapeutic effect and/or monitoring recurrence in a cancer patient.

BACKGROUND ART

Cancer is versatile, so that no effective fixed treatment protocol has been established. It seems important to specify a personalized specific treatment protocol. Thus, it is a critical issue in cancer treatment to evaluate therapeutic effects of the cancer treatment. In addition, although cancer of interest appears to be temporarily removed by treatment, cancer that has not been completely excised by surgery remains in some cases. It is important to evaluate these matters from the viewpoints of preventing recurrence or selecting a treatment protocol prepared for recurrence.

Biomarkers have been developed that indicate the presence of cancer. Unfortunately, cancer is versatile, so that there is a maker-specific limit for its detectability and sensitivity. Consequently, other indicators that each indicate the presence of cancer are needed. Besides, another issue is that in diagnostic imaging, cancer cannot be detected unless the cancer grows to a certain size or more.

CITATION LIST

Patent Literature

Patent Literature 1: WO 2015/088039

SUMMARY OF INVENTION

The present invention provides a method for predicting a therapeutic effect and/or monitoring recurrence in a cancer patient.

The present inventor has found that prediction of therapeutic effects and/or monitoring of recurrence in cancer patients are made possible by evaluating nematode tactic behavior to urine from a patient with cancer. The present invention is based on such findings.

Specifically, the present invention provides the following aspects.

(1) A method for detecting a therapeutic effect of cancer treatment in a cancer patient, comprising:
evaluating nematode tactic behavior to each of pre-treatment urine and in-treatment or post-treatment urine from the cancer patient; and
comparing a result of measuring the tactic behavior to the pre-treatment urine and a result of measuring the tactic behavior to the in-treatment or post-treatment urine, wherein
when attraction is weakened or avoidance is strengthened after the treatment, it is determined that the therapeutic effect is detected.

(2) The method according to the above (1), wherein when attraction to the pre-treatment urine is exhibited and avoidance to the post-treatment urine is exhibited, it is determined that the therapeutic effect is detected.

(3) The method according to the above (1), wherein when attraction to the pre-treatment urine is exhibited and avoidance to the post-treatment urine is not exhibited, it is determined that there is no therapeutic effect or the therapeutic effect is poor.

(4) A method for detecting proliferation of cancer in a cancer patient after treatment, comprising:
evaluating nematode tactic behavior to a time-series of urine from the cancer patient, wherein
it is determined that the proliferation of cancer is detected when avoidance to the urine from the cancer patient is weakened or attraction thereto is strengthened as the time-series for evaluating results obtained progresses.

(5) The method according to the above (4), wherein it is determined that the proliferation of cancer is detected when the tactic behavior to the urine from the cancer patient is changed from avoidance to attraction as the time-series for evaluating results obtained progresses.

(6) A method for detecting a therapeutic effect of cancer treatment and proliferation of cancer after the treatment in a cancer patient, comprising
evaluating nematode tactic behavior to each of pre-treatment urine and in-treatment or post-treatment urine from the cancer patient and
comparing a result of measuring the tactic behavior to the pre-treatment urine and a result of measuring the tactic behavior to the in-treatment or post-treatment urine, wherein
when attraction is weakened or avoidance is strengthened after the treatment, it is determined that the therapeutic effect is detected; and further comprising
evaluating nematode tactic behavior to a time-series of urine from the cancer patient after the treatment, wherein
it is determined that the proliferation of cancer is detected when avoidance to the urine from the cancer patient is weakened or attraction thereto is strengthened as the time-series for evaluating results obtained progresses.

(6B) A method for monitoring proliferation of cancer or monitoring recurrence of cancer, comprising
evaluating nematode tactic behavior to a time-series of urine from an in-treatment or post-treatment cancer patient, wherein
it is determined that the proliferation of cancer is detected or the recurrence of cancer is detected when avoidance to the urine from the cancer patient is sequentially weakened or attraction thereto is sequentially strengthened as the time-series for evaluating results obtained progresses.

(6C) A method for monitoring proliferation of cancer or monitoring recurrence of cancer, comprising
observing nematode tactic behavior to a time-series of urine from an in-treatment or post-treatment cancer patient, and
detecting that avoidance to the urine from the cancer patient is sequentially weakened with the lapse of time and/or detecting that attraction thereto is sequentially strengthened with the lapse of time, whereby it is determined that the cancer proliferates or the cancer recurs.

(7) A composition comprising nematode worms used for evaluating a therapeutic effect of cancer treatment.

(8) A composition comprising nematode worms used for predicting or monitoring recurrence of cancer after treatment.

BRIEF DESCRIPTION OF DRAWING

FIG. 1 shows the pre-operation and post-operation history and the results of recurrence monitoring in a cancer patient by a urine test using nematode worms.

DESCRIPTION OF EMBODIMENTS

As used herein, the "subject" means a mammal such as primates (e.g., a monkey, chimpanzee, gorilla, bonobo, orangutan, marmoset, human) and means, for instance, a human. As used herein, the subject is preferably a human. In addition, as used herein, the word "subject" is used, in a sense, to include a healthy individual, a subject suspected of having cancer, and a subject suffering from cancer.

As used herein, the "cancer" means malignant tumor. Cancer can be largely grouped into hematopoietic tumor, carcinoma, and non-epithelial sarcoma (sarcoma). Examples of the hematopoietic tumor include leukemia, malignant lymphoma, and myeloma. Examples of the carcinoma include lung cancer, breast cancer, gastric cancer, colon cancer, uterine cancer, ovarian cancer, head and neck cancer, and tongue cancer. Examples of the sarcoma include osteosarcoma, chondrosarcoma, rhabdomyosarcoma, leiomyosarcoma, fibrosarcoma, liposarcoma, and angiosarcoma. As used herein, the "cancer" encompasses early cancer such as stage 0 early cancer and stage 1 early cancer.

As used herein, the wording "detecting a therapeutic effect of cancer treatment" can be read as the wording "evaluating a therapeutic effect of cancer treatment", "predicting a therapeutic effect of cancer treatment", "diagnosing a therapeutic effect of cancer treatment", or "non-diagnostically helping diagnose a therapeutic effect of cancer treatment".

As used herein, the wording "detecting proliferation of cancer" in the post-operation context can be read as the wording "detecting a possibility of recurrence", "predicting recurrence", "predicting a possibility of recurrence", or "evaluating a possibility of recurrence".

As used herein, the "recurrence" refers to a phenomenon where although a therapeutic effect appears to be exerted, cancer then occurs at the same site or another site. That is, the word "recurrence" is used, in a sense, to include metastasis. The "recurrence" may also be called "relapse".

As used herein, the "nematode" means *Caenorhabditis elegans*. In the *Caenorhabditis* Genetics Center (CGC) of College of Biological Sciences, University of Minnesota, nematode strains isolated from various environments are stored, open to the public, and available on request. Thus, those skilled in the art can acquire almost any known strains from the CGC. From the viewpoint of reproduction through self-fertilization, hermaphrodites may be preferably used.

As used herein, the "tactic behavior" means attraction behavior or avoidance behavior. The attraction behavior means a behavior of making shorter the physical distance to a certain substance. The avoidance behavior means a behavior of making longer the physical distance to a certain substance. An attraction behavior-inducing substance is called an attractant. An avoidance behavior-inducing substance is called a repellent. nematode has characteristics such as approaching to an attractant and escaping from a repellent based on the olfaction thereof. A behavior of approaching to an attractant is referred to as attraction behavior (as used herein, sometimes referred to as "positive"). A behavior of escaping from a repellent is referred to as avoidance behavior (as used herein, sometimes referred to as "negative"). In addition, the attraction behavior and the avoidance behavior are collectively called as tactic behavior.

As used herein, the "wild-type strain" is a nematode wild-type strain. Examples include a common wild-type N2 Bristol strain. The wild-type strain as used herein may be a strain by which attraction to urine obtained from each subject with cancer is exhibited and avoidance to urine obtained from each subject without cancer is exhibited.

Method of Analyzing Urine by Using System for Evaluating Nematode Tactic Behavior A method of analyzing urine by using a system for measuring nematode tactic behavior can be put into practice by placing nematode worms at a certain distance from a test sample (e.g., urine) obtained from a subject and observing whether the worms exhibit attraction behavior to the test sample or exhibit avoidance behavior thereto. Then, when the attraction behavior is exhibited, the subject can be evaluated as suffering from cancer or as having a possibility of suffering from cancer. Accordingly, WO 2015/088039 discloses that in a medium-scale study of 242 test subjects, cancer patients were successfully detected with 100% sensitivity and 95% specificity.

More specifically, the method for analyzing urine by using a system for measuring nematode tactic behavior may comprise: for instance, placing, on a dish (e.g., a dish on which a solid medium is introduced), a test sample (e.g., urine) obtained from a subject;

placing, on the dish on which the test sample is placed, nematode worms positioned at a certain distance from the test sample;

letting the worms behave after the placement; and evaluating that the subject suffers from cancer or may suffer from cancer when the worms exhibit attraction behavior to the test sample.

nematode tactic behavior can be evaluated by determining the difference and/or the ratio between the number of worms attracted to the test sample and the number of worms repelled from the test sample. The difference in the number of worms may be used for assessment. When the difference is a positive value, the test sample as a whole induces attraction behavior and can be assessed that the test sample is derived from a cancer patient. When the difference is a negative value, the test sample as a whole induces avoidance behavior and can be assessed that the test sample is derived from a healthy individual. In addition, the nematode tactic behavior can be measured by using, for instance, the following tactic behavior index as an indicator.

$$\text{(Tactic index)} = \frac{A - B}{A + B} \quad \text{[Expression 1]}$$

wherein, A represents the number of worms exhibiting attraction to a test sample; and B represents the number of worms exhibiting avoidance to the test sample.

If the tactic index is a positive value, the test sample as a whole induces attraction behavior and can be assessed that the test sample is derived from a cancer patient. If the tactic index is a negative value, the test sample as a whole induces avoidance behavior and can be assessed that the test sample is derived from a healthy individual.

As the tactic index is closer to 1, the percentage of worms exhibiting attraction behavior is indicated to be larger. As the tactic index is closer to −1, the percentage of worms exhibiting avoidance behavior is indicated to be larger. If the tactic index is closer to 0, it is interpreted that the worms exhibit neither attraction behavior nor avoidance behavior. The larger the absolute value for the tactic index, the clearer the behavior assessment results.

The present inventor has found that there is a sharp change in nematode tactic behavior to urine from each cancer patient, who has received treatment, between before and after the treatment of cancer. Accordingly, the present inventor has found that, based on the nematode tactic behavior to urine from each cancer patient before and after treatment, therapeutic effects of the cancer treatment can be evaluated. The present inventor has also found that, based on the nematode tactic behavior to urine from each post-treatment cancer patient, recurrence of cancer can be predicted.

The present invention can provide a method for evaluating (or a method for predicting, a method for detecting, or a method for diagnosing, or a method for acquiring basic information about) a therapeutic effect of cancer treatment in a cancer patient, wherein based on nematode tactic behavior to each of pre-treatment urine and post-treatment urine from a cancer patient, an therapeutic effect of the cancer treatment is evaluated (or predicted, detected, or diagnosed). The above method makes it possible to observe how the nematode tactic behavior changes between before and after the treatment by measuring nematode tactic behavior to each of pre-treatment urine and in-treatment or post-treatment urine from the cancer patient; and comparing a result of measuring the tactic behavior to the pre-treatment urine and a result of measuring the tactic behavior to the in-treatment or post-treatment urine. Optionally, the results of measuring the tactic behavior between before and after the treatment can be output.

As used herein, the "pre-treatment" means a time before cancer treatment to be evaluated. For instance, during three-months treatment, therapeutic effects from one month to two months after initiation of the treatment may be evaluated. In this case, the cancer treatment to be evaluated is "treatment from one month to two months after initiation of the treatment". Accordingly, the "pre-treatment" in this case refers to one month after initiation of the treatment and the pre-treatment urine is urine obtained at one month after initiation of the treatment. That is, the term "pre-treatment" does not necessarily mean a time before initiation of a series of treatment, but sometimes means a time during treatment. Thus, the term is a relative term meaning a time before initiation of cancer treatment to be evaluated.

As used herein, the "in-treatment" means a time amid cancer treatment to be evaluated.

As used herein, the "post-treatment" means a time after cancer treatment to be evaluated. For instance, during three-month treatment, therapeutic effects from one month to two months after initiation of the treatment may be evaluated. In this case, the cancer treatment to be evaluated is "treatment from one month to two months after initiation of the treatment". Accordingly, the "post-treatment" in this case refers to treatment at two months after initiation of the treatment and the post-treatment urine is urine obtained at two months after initiation of the treatment. That is, the term "post-treatment" does not necessarily mean a time after completion of a series of treatment, but sometimes means a time during treatment (e.g., a case where after the treatment, another cancer therapy continues). Thus, the term is a relative term meaning a time after completion of cancer treatment to be evaluated.

The observation results are used to determine (or predict, detect, or diagnose) that a therapeutic effect has been exerted when attraction behavior is weakened or avoidance behavior is strengthened after the treatment. In addition, the observation results are used to determine (or predict, detect, or diagnose) that a therapeutic effect has been exerted when attraction behavior to pre-treatment urine is exhibited and avoidance behavior to post-treatment urine is exhibited. Alternatively, the observation results are used to determine (or predict, detect, or diagnose) that no therapeutic effect has been exerted or the therapeutic effect has been poor when attraction behavior to pre-treatment urine is exhibited and avoidance behavior to post-treatment urine is not exhibited.

For instance, when therapeutic effects of cancer treatment are evaluated, there is sometimes a case where treatment A is implemented by a certain time point and is switched to treatment B after the certain time point or treatment B in combination is started after the certain time point. The treatment protocol may be changed in this fashion. At that time, the present invention may also be used to determine which of the treatment protocols is preferable by comparing the therapeutic effects between before and after the change. From this viewpoint, the present invention provides a method for evaluating whether a treatment protocol is good or poor, comprising:

[1] evaluating nematode tactic behavior to each of pre-treatment urine and in-treatment or post-treatment urine from a cancer patient between before and after a first treatment protocol and comparing a result of evaluating the tactic behavior to the pre-treatment urine and a result of measuring the tactic behavior to the in-treatment or post-treatment urine;

[2] evaluating nematode tactic behavior to each of pre-treatment urine and in-treatment or post-treatment urine from the cancer patient between before and after a second treatment protocol and comparing a result of measuring the tactic behavior to the pre-treatment urine and a result of evaluating the tactic behavior to the in-treatment or post-treatment urine; and

[3] comparing a therapeutic effect of the first treatment protocol and a therapeutic effect of the second treatment protocol.

According to the present inventor, provided is a method for evaluating (or a method for determining, a method for predicting, a method for detecting, or a method for diagnosing) proliferation of cancer (or volume of cancer) in vivo in a cancer patient after treatment, wherein the proliferation of cancer (or volume of cancer) is evaluated (or determined, predicted, detected, or diagnosed, or basic information about a therapeutic effect is acquired) based on nematode tactic behavior to a time-series of urine from the cancer patient. In the above method, a time-series of urine collected from a post-treatment cancer patient is prepared and how the nematode tactic behavior to each urine is changed can be observed. Optionally, the results of measuring the tactic behavior to the time-series of urine can be output.

The observation results are used to evaluate (or determine, predict, detect, or diagnose) that the cancer has proliferated (or the cancer volume has increased) when avoidance behavior to the urine from the cancer patient is weakened or attraction behavior thereto is strengthened as the time-series for the above urine samples progresses. Alternatively, the observation results are used to evaluate (or determine, predict, detect, or diagnose) that the cancer has proliferated (or the cancer volume has increased) when the tactic behavior to the urine from the cancer patient has been changed from avoidance behavior to attraction behavior as the above time-series progresses.

From the viewpoints of cancer proliferation monitoring and cancer recurrence monitoring, the time-series for urine samples may be a periodically scheduled time-series. For instance, the urine samples may be collected with an interval of from 1 week to 1 year, for example, once every 1 week, once every 2 weeks, once every 3 weeks, once every 4 weeks, once every 1 month, once every 2 months, once every 3 months, once every 4 months, once every 5 months, once every 6 months, or once every 1 year. Alternatively, urine may be collected non-periodically when cancer proliferation or recurrence, for instance, is suspected or needed to be checked. Urine may be collected at the time of periodical urine collection as well as when cancer proliferation and/or recurrence is suspected. As used herein, the "time-series" is used for a plurality of samples collected at two or more different time-points. Accordingly, two or more, three or more, or four or more urine samples may be included in the time-series. If the results of measuring tactic behavior to three or more urine samples are compared, an advantage is that the trend of change (e.g., a change) in tactic behavior is easy to understand.

The above method for evaluating (or method for predicting, method for detecting, or method for diagnosing, or method for acquiring basic information about) an therapeutic effect of cancer treatment may be implemented further in combination with the method for evaluating (or method for determining, method for predicting, method for detecting, or method for diagnosing, or method for acquiring basic information about a therapeutic effect on) proliferation of cancer (or the volume of cancer) in vivo in a cancer patient after treatment. Specifically, a pre-treatment urine sample from a cancer patient and a post-treatment urine sample from the cancer patient are used to evaluate therapeutic effects of the cancer treatment, and then, the proliferation of cancer and/or the volume of cancer in vivo in the cancer patient may be evaluated from a time-series of urine samples (see, for example, FIG. 1).

The present invention provides a composition comprising nematode worms used for evaluating a therapeutic effect of cancer treatment. This composition may be used for the above-described methods.

The present invention provides a composition comprising nematode worms used for predicting or monitoring recurrence of cancer after treatment.

EXAMPLES

Example 1: Surgical Removal and Recurrence of Tumor

The present inventor has since revealed that nematode exhibits attraction behavior to urine from cancer patients. In this Example, further investigated was how the nematode attraction behavior was associated with removal and recurrence of tumor in a particular cancer patient.

The cancer patient with a very low level of each tumor marker, which was negative in a tumor marker test, was monitored.

The above cancer patient, whose tumor was removed and then recurred, had the following history.

TABLE 1

| Date | Events |
| --- | --- |
| February 2015 | Sigmoid colon cancer was found to be metastasized into the lung (right middle lobe) (stage 1a colon cancer) |
| April 2015 | Surgical removal of primary lesion and metastatic lesion |
| August 2015 | No matters of concern were found in a blood test or a CT test. |
| November 2015 | No matters of concern were found in a blood test or a CT test. |
| End of February 2016 | Recurrence in the lung (right lower lobe) was found by a CT test. |

Urine was sampled from the above patient once every about 1 month from nearly the date of operation in April 2015 and was frozen and stored.

Next, how nematode tactic behavior was associated with each urine derived from the above patient was examined. The tactic behavior was measured as described in WO 2015/088039. FIG. 1 shows the results.

As shown in FIG. 1, after the surgical removal of tumor, attraction behavior to urine from the cancer patient disappeared and avoidance behavior appeared. Immediately after the operation, in particular, a big change in the nematode tactic behavior to urine was already detected. Meanwhile, the day when the recurrence of cancer was detected by CT is Feb. 28, 2016. The nematode worms exhibited, by the end of September 2015, about 5 months before the day, attraction behavior to urine from the above patient. Further, it was also observed that avoidance behavior was weakened over from May to August 2015 before the recurrence.

This result indicates that the concentration of nematode attractant in urine from the cancer patient was very rapidly changed after the removal of cancer. This has revealed that the degree of surgical removal of cancer can be accurately checked by the urine test using nematode worms.

In addition, the nematode worms detected an in-urine attractant at several months before the recurrence was found by CT, which made it possible to predict the recurrence in the patient. This has demonstrated that the cancer patient urine test using nematode worms is useful in evaluating recurrence and/or outcomes of cancer.

Example 2: Urine Test Using Nematode Worms Before and after Operation and Chemotherapy In this Example, the results of Example 1 were reproduced by increasing the number of test subjects markedly.

Urine before and after operation and chemotherapy was collected from each patient with colon cancer, gastric cancer, pancreatic cancer, esophageal cancer, bile duct cancer, or gallbladder cancer, and was frozen and stored. One month after the treatment, urine was collected from 45 test subjects. Three months after the treatment, urine was collected from 15 test subjects.

nematode tactic behavior to each urine collected was evaluated like Example 1.

As a result, it was observed that in 31 of 45 test subjects (68.9%), the index changed to negative at 1 month after the treatment (i.e., changed from attraction behavior to avoidance behavior). It was also observed that in 10 of 15 test subjects (66.7%), the index changed to negative at 3 months after the treatment.

In this way, the nematode worms changed their tactic behavior from attraction behavior to avoidance behavior between before and after the treatment of each patient with different cancer. This change in tactic behavior seems to result from the phenomenon where nematode sharply detects and responds to a change, between before and after the treatment, in the level of an attractant contained in urine from each cancer patient.

Cases of the above patients include an instance where a cancerous tissue cannot be completely removed by treatment and a case where cancer has already metastasized.

The above results have demonstrated that the cancer patient urine test using nematode worms is useful in evaluating treatment.

The invention claimed is:
1. A method for detecting proliferation of cancer in a cancer patient after treatment, comprising:

providing a nematode a distance from each of at least two urine samples from the cancer patient to induce taxis behavior of the nematodes, performing chemotaxis assay using the nematode to observe nematode taxis behavior to each of the samples, wherein the at least two urine samples from the patient are obtained within the first 10 months after the treatment at a time interval of from one week to three months and before the proliferation of cancer becomes detectable with computed tomography, and the proliferation of cancer is detected when avoidance to the urine samples from the cancer patient is weakened or attraction thereto is strengthened during the interval.

2. The method according to claim 1, the proliferation of cancer is detected when the taxis behavior to the urine samples from the cancer patient is changed from avoidance to attraction during the time interval.

3. The method according to claim 1, further comprising outputting that the proliferation of cancer is detected when avoidance to the urine samples from the cancer patient is weakened or attraction thereto is strengthened during the interval, and further comprising outputting that the proliferation of cancer is not detected when avoidance to the urine samples from the cancer patient is not weakened or attraction thereto is not strengthened during the interval.

* * * * *

UNITED STATES PATENT AND TRADEMARK OFFICE
CERTIFICATE OF CORRECTION

| | |
|---|---|
| PATENT NO. | : 12,019,068 B2 |
| APPLICATION NO. | : 16/498895 |
| DATED | : June 25, 2024 |
| INVENTOR(S) | : Takaaki Hirotsu |

It is certified that error appears in the above-identified patent and that said Letters Patent is hereby corrected as shown below:

On the Title Page

Item (71) should read:
- (71) Applicants: HIROTSU BIO SCIENCE INC., Chiyoda-ku (JP);
             NANPUH HOSPITAL, Kagoshima (JP)

Signed and Sealed this
Thirteenth Day of August, 2024

Katherine Kelly Vidal
*Director of the United States Patent and Trademark Office*